United States Patent [19]

Anderson

[11] Patent Number: 5,098,536

[45] Date of Patent: Mar. 24, 1992

[54] METHOD OF IMPROVING SIGNAL-TO-NOISE IN ELECTROPHEROGRAM

[75] Inventor: Philip D. Anderson, Fullerton, Calif.

[73] Assignee: Beckman Instruments, Inc., Fullerton, Calif.

[21] Appl. No.: 649,393

[22] Filed: Feb. 1, 1991

[51] Int. Cl.$^5$ .................. B01D 57/02; B01D 61/42
[52] U.S. Cl. .................. 204/180.1; 204/299 R; 356/344
[58] Field of Search .................. 204/299 R, 180.1; 356/344; 435/6; 436/516; 364/496

*Primary Examiner*—John Niebling
*Assistant Examiner*—Caroline Koestner
*Attorney, Agent, or Firm*—William H. May; Paul R. Harder; Wen Liu

[57] ABSTRACT

A method and apparatus for improving signal to noise in an electropherogram acquired by electrophoresis. The migration time is remapped by binning the data with respect to migration time to improve signal to noise and peak resolution. The data points of the electropherogram are pooled into variable size bins, each corresponding to a number of time intervals. The sizes of the bins increase with migration time. To further improve signal to noise and peak resolution, the binned data is filtered by Fourier transformation. The present invention allows for accurate determinatiion of DNA sequences.

20 Claims, 3 Drawing Sheets

METHOD OF IMPROVING SIGNAL-TO-NOISE IN ELECTROPHEROGRAM

BACKGROUND OF THE INVENTION

1. Field of the Invention

The present invention relates generally to the field of electrophoresis and more particularly to a method for improving signal-to-noise in the electropherogram acquired by capillary electrophoresis.

2. Description of Related Art

Capillary electrophoresis is a high resolution, high sensitivity method for the separation and detection of molecular species such as peptides, proteins, and oligonucleotides (analytes). Separation is carried out in the capillary by causing the analytes to migrate at different rates in a separation medium (gel or electrolyte solution) under the influence of an electric field. Analytes of the same species are resolved into respective bands as separation takes place. A detector detects the presence of the bands. Detection can be by one of several schemes, including laser-induced fluorescence (see U.S. Pat. No. 4,675,300 to Zare), absorbance and radioactivity detection.

Typically, the results of detection is represented by a plot of detected intensity versus time, a so-called electropherogram. As the species migrate past the detector, it produces a peak in the electropherogram. By analyzing the electropherogram, one may be able to identify the presence of a particular species. Also, one may be able to identify the sample that underwent electrophoresis by looking at the distribution of the species as represented by the electropherogram (for example in identifying a DNA sample by analyzing data obtained from electrophoresis of sequenced DNA fragments).

FIG. 1 shows an electropherogram between 4400 and 4800 seconds of migration using an arbitrary zero reference time when data was first taken during electrophoresis. Data was collected at every 0.1 second. There is a total of 4,000 data points in the plot. It can be seen that for the entire duration of data acquisition, a large set of date points are obtained. Accordingly, the data storage requirement is substantial. Also, as can be seen in FIG. 1, the use of 0.1 second digitization results in a plot with rough lines and poor peak resolution. Better resolution can be obtained but is impractical as substantially more data storage space would be required. It is also difficult to determine whether some of the peaks actually represent the presence of separated molecular species or are in fact noise. In fact, the signal-to-noise ratio is poor for region of low signal. An improved method to increase signal-to-noise as well as resolution of the detection peaks is desired.

SUMMARY OF THE INVENTION

The present invention is directed to a method for remapping the migration time to improve signal-to-noise and resolution with respect to identification of peaks in an electropherogram. The data points of the electropherogram are pooled into variable size bins, each corresponding to a number of time intervals having upper and lower limits that together span a predetermined range of time. The size of the bins increases with migration time.

In one embodiment of the present invention, the number of time intervals per bin is determined according to an arithmetic series of integer numbers wherein the difference between consecutive bins is a constant. The value of the data points within the time intervals belonging to a bin are summed to represent the total value for the particular bin. The resulting electropherogram is represented with respect to a square root scale, where the average migration time of each window is approximately proportional to the square of the corresponding bin number.

In another aspect of the present invention, the binned data can be Fourier transformed to data that can be easily interpreted to identify peaks.

DESCRIPTION OF ILLUSTRATED EMBODIMENTS

The following description is of the best presently contemplated mode of carrying out the invention. This description is made for the purpose of illustrating the general principles of the invention and should not be taken in a limiting sense. The scope of the invention is best determined by reference to the appended claims.

Figure 2:
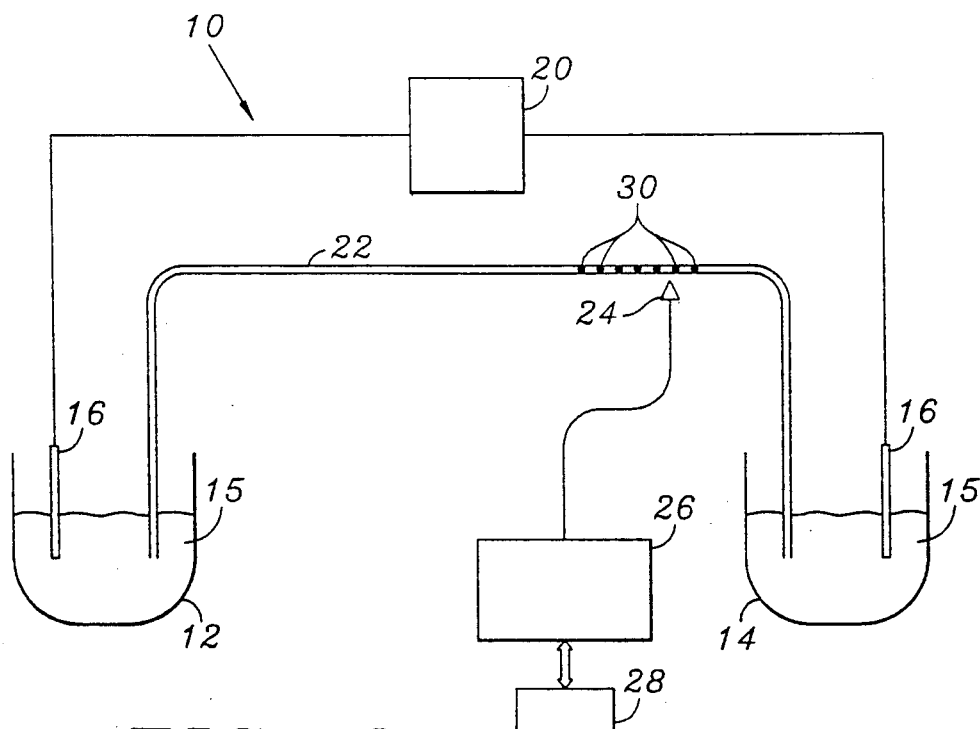
FIG. 2 is a schematic diagram of a electrophoresis system in which the present invention can be incorporated.

With reference to FIG. 2, an electrophoretic system 10 is schematically shown. The system 10 comprises two containers 12 and 14 containing electrolyte 15, electrodes 16 and 18, a high voltage source 20, a capillary 22, a detector 24 and associated data acquisition hardware, and a computing unit 26 having data memory 28. To carry out electrophoresis, the capillary 22 is filled with electrolyte and a sample is introduced into one end of the capillary. The ends of the capillary 22 are submerged in the electrolyte 15 to complete a electrical circuit in conjunction with the electrolyte 15, electrodes 16 and 18 and the high voltage source 20. Under applied voltage, the sample will separate into its molecular species. The species are resolved into bands 30 as separation takes place. The bands 30 migrate along the capillary and past the detector 24 in sequence. Detection can be accomplished by for example laser-induced fluorescence, absorbance or radioactivity detection. These and other detection techniques have been well documented in the literatures. Data is taken at regular intervals (e.g. 0.1 second), consequently obtaining data at discrete data points. The data is sorted by the computing unit 26 into bins of different migration time intervals. The bin size increases with migration time. More particularly, the computing unit compares the migration time for each data to a plurality of predetermined values which define a plurality of time interval ranges or bins that together span a predetermined overall migration time range. According to the migration time, the computing unit determines which bin the data falls within and accordingly sums the value of the data to the total value stored in the bin. The memory 28 includes a plurality of storage locations corresponding to the number of bins established by the computing unit 26.

At the end of data acquisition, the memory 28 is accessed by the computing unit 26 for visual representation of the data in the form of an electropherogram. A display unit such as a conventional cathode ray tube or a printer (not shown) may be used. Specifically, the computing unit 26 processes the total value in each bin to obtain an average value for the total time interval of that bin.

In accordance with one embodiment of the present invention, the total time intervals for each bin are different from each other and are determined by the computing unit 26 according to a square root relationship in which the mean migration time within a particular bin is proportional to the square root of the number of that bin. It has been found that such a relationship is satisfied when the widths of the bins, i.e. the number of unit time intervals for the respective bins, follow an arithmetic series in which the difference in number of unit time intervals for consecutive bins is an integer constant.

The mathematical analysis is shown below.

Let

N = total number of bins n = 1, 2, 3, ---, N, the consecutive numbers of the bins $I_n$ = number of time interval units in the nth bin $\delta I$ = difference in number of time interval units between consecutive bins (a constant)

$T_n$ = upper limit of migration time of nth bin $\overline{T}_n$ = mean migration time of the nth bin $\delta t$ = the width of each time interval unit (a constant)

Figure 3:
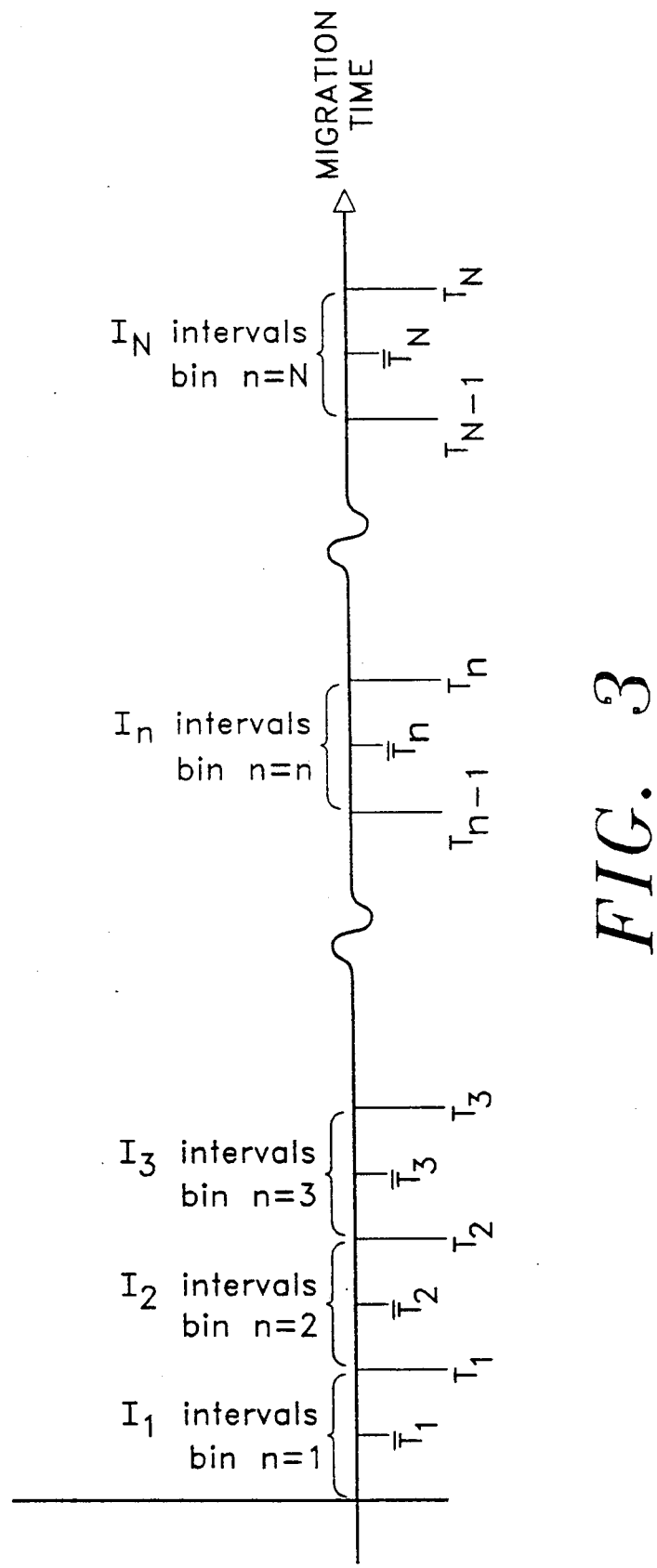
FIG. 3 is a schematic representation of the data bins in accordance with one embodiment of the present invention.

FIG. 3 depicts a schematic illustration of the bins of migration time.

$I_n$ follows an arithmetic series having difference $\delta I$. The number of time interval units in the ith bin is given by:

$$I_i = I_1 + (i-1)\delta I \tag{1}$$

and the total number of unit time interval in the first n windows is given by:

$$\sum_{i=1}^{n} I_i = nI_1 + \tfrac{1}{2}n(n-1)\delta I \tag{2}$$

based on the well known relationship $$\sum_{1}^{n}(i-1) = \tfrac{1}{2}n(n-1)$$

[Example: 0 + 1 + 2 + 3 = 6 = ½(4)(3)]

It follows that:

$$T_n = \delta t \sum_{i=1}^{n} I_i \tag{3}$$

$$\overline{T}_n = (T_n + T_{n-1})/2 \tag{4}$$

$$= \frac{\delta t}{2}\left(\sum_{i=1}^{n} I_i + \sum_{i=1}^{n-1} I_i\right)$$

Substituting equation (2) into (4) and simplifying gives:

$$\overline{T}_n = \frac{\delta t}{2}[(n^2 - 2n + 1)\delta I + (2n - 1)I_1] \tag{5}$$

It can be seen that when n is large, $\overline{T}_n$ can be expressed approximately as:

$$\overline{T}_n = An^2 + B \tag{6}$$

where A and B are constants. B can be set equal to zero by measuring time from some arbitrary point.

Thus, it can be said the average migration time in bin n is proportional to the square of the bin number and can be expressed approximately as:

$$\overline{T}_n \propto n^2 \tag{7}$$

or $$n \propto \sqrt{\overline{T}_n} \tag{8}$$

The constants $\delta t$ and $\delta I$ are chosen according to the expected full range values of migration time and the desired resolution. The maximum number of bins is dependent on $\delta I$ and the number of memory locations available. Referring to equation (5), constants A and B are dependent on $\delta t$, $\delta I$ and $I_1$.

Figure 1:
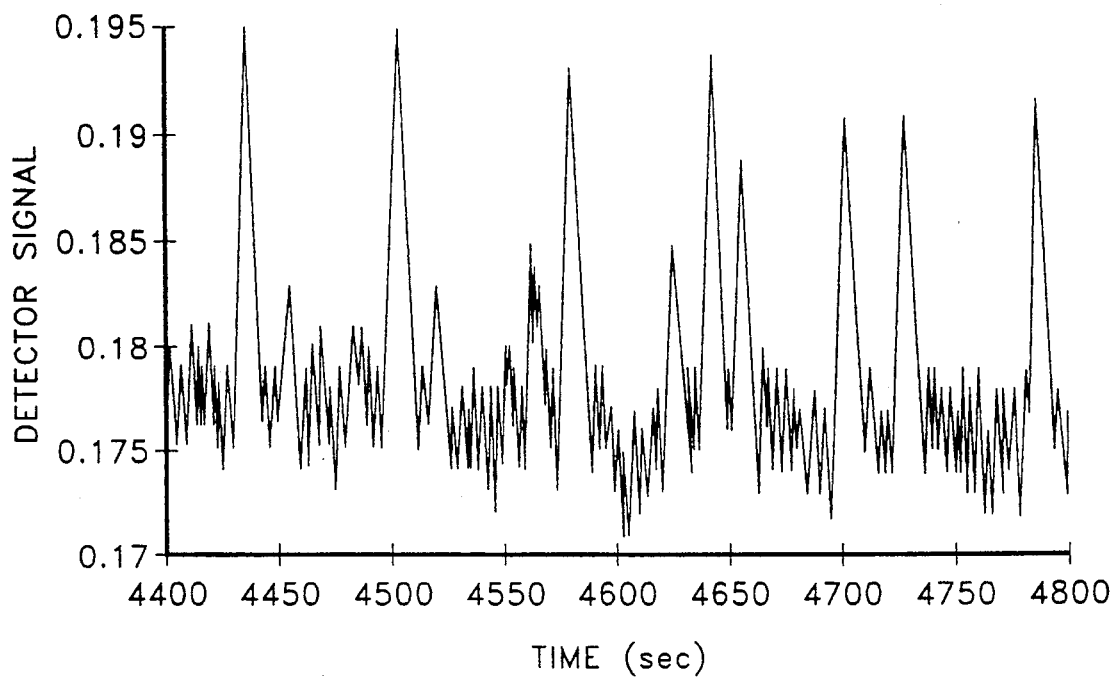
FIG. 1 is an actual electropherogram plotted with raw data obtained from electrophoresis of a sample.
Figure 4:
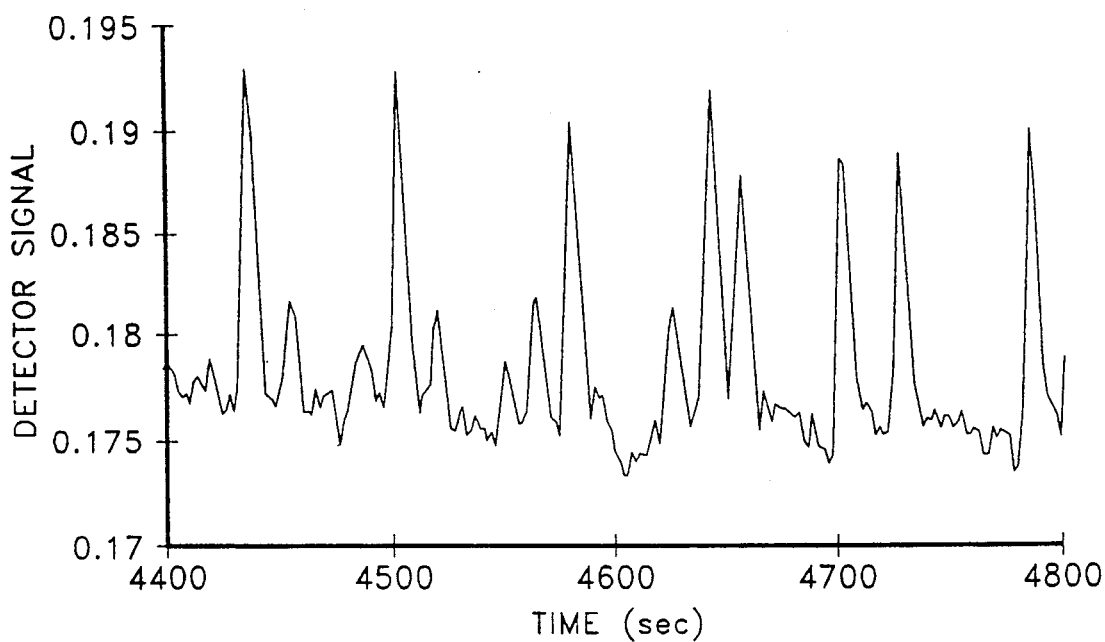
FIG. 4 is an electropherogram showing data replotted with binned data.

FIG. 4 represents an electrogram produced from data points that have been binned in accordance with the above-described method. As compared to FIG. 1, the number of binned data points are 120 instead of 4,000. This means a substantial savings in memory space. It follows that more data can be taken for a larger overall migration time interval, i.e. electrophoresis of longer duration. Comparing FIG. 4 to FIG. 1, the binning method of the present invention actually filters out noise present in FIG. 1. Peaks in the electropherogram is more clearly defined in FIG. 4. One can therefore obtain more accurate interpretation of the result of the electrophoresis separation.

In view of the foregoing, it can be seen that by using a square root representation, better resolution and signal-to-noise can be achieved.

In the past, in order to increase the resolution for low data values on the electropherogram, the rate of data acquisition must be increased (i.e. increasing the number of data points per second) which accordingly increases the number of memory storage locations and data processing time. Even by doing so, the poor signal-to-noise for low data values is still a problem. By utilizing a square root representation of migration time according to the present invention, the resolution of the electropherogram is increased and signal-to-noise improved without sacrificing memory storage locations. In fact, the present invention accomplishes such advantages by more efficiently using available memory storage locations. It is understood that if one can meet data storage requirements, one can store the raw data from the detector and then subsequently perform noise filtering by binning described herein.

Figure 5:
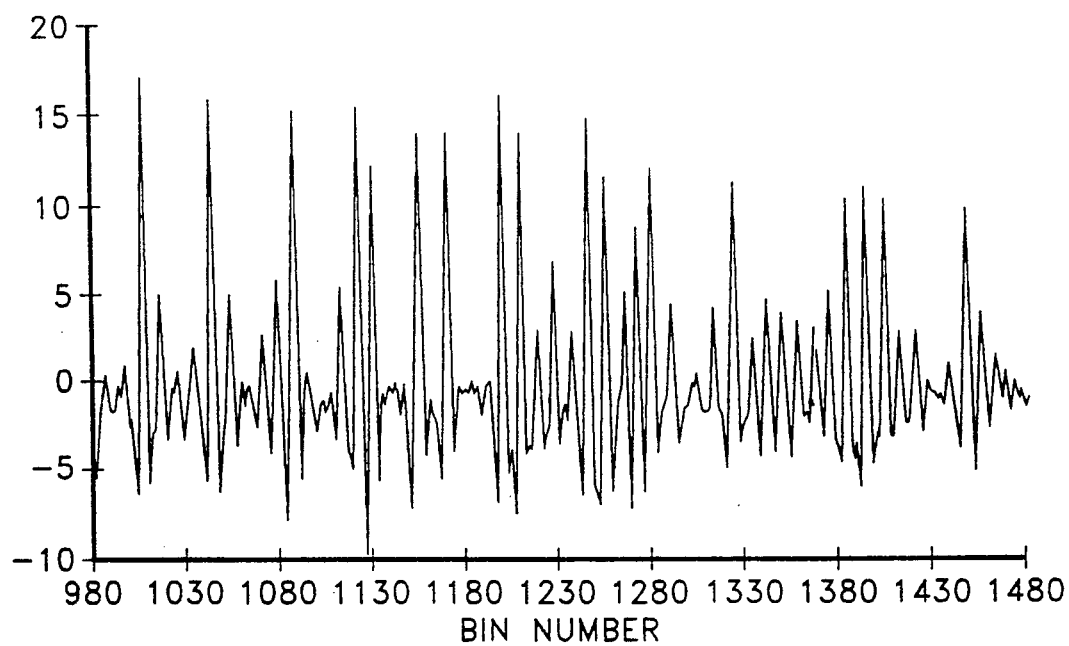
FIG. 5 is a plot of a Fourier transformed electropherogram.

A further advantage of the present invention is that the binned data can be Fourier transformed for further data analysis. The electropherogram plotted using binned data results in peaks of approximately equal band width and spacing. (While it is not clear from FIG. 1, the band width and spacing of the peaks in the raw data have been found to increase slightly with migration time.) This greatly facilitates subsequent data analysis by Fourier transformation. FIG. 5 shows a Fourier transformed representation of an electropherogram plotted against the bin number. Fourier transformation techniques are well known in the art and will not be discussed herein. Referring to FIG. 5, it can be seen that signal-to-noise is further improved by Fourier transformation. Most of the background noise and baseline drift have been removed by the transformation. It has been determined that peaks having amplitudes above the zero axis are corresponding to the presence of species, data and peaks appearing below the zero axis are derived from noise. Without undue experimentation an offset may be applied to adjust the reference the zero axis.

The present invention can be applied advantageously to DNA sequencing analysis. DNA sequencing has been widely practiced to obtain DNA fragments from which the DNA sample may be identified. Documentation of the sequencing techniques are widely available. There are several well known approaches to DNA sequence determination. In general, the techniques involve generating DNA fragments of progressively increasing lengths. Each fragment terminates in one of four nucleotides. One of several types of tagging schemes may be used to assign a signature to each fragment. The detector response to the tagged gel fragments may be different. By way of example, flour materials may be used for tagging to allow flourescence detection. For fragments that are separated by electrophoresis as described herein, the longer fragments migrate at a slower rate. As the fragments migrate past the detector, the fragments are detected by the detection of the flour materials, thereby forming a peak in the data. Because the detector response may be different for different tagged fragments, the terminating nucleotide can be determined. (The example in FIGS. 1, 4 and 5 were obtained from electrophoresis of DNA fragments.) One can then identify the sequence of terminating nucleotides for progressively longer fragments, thereby allowing identification of the DNA sample.

Accordingly, the importance of good peak resolution and signal to noise in electrophoresis of DNA fragments is critical to a positive identification of the DNA sample. The method of the present invention can be used to filter the raw data from the detector to improve signal-to-noise as well as the peak resolution.

While the invention has been described with respect to the illustrated embodiments in accordance therewith, it will be apparent to those skilled in the art that various modifications and improvements may be made without departing from scope and spirit of the invention. Accordingly, it is to be understood that the invention is not to be limited by the specific illustrate embodiments, but only by the scope of the appended claims.

I claim:

1. A method of analyzing data with respect to migration time obtained from an electrophoresis process comprising the steps of:
   choosing a plurality of bins each of a size corresponding to a range of migration time, wherein the sizes of the bins increases progressively at higher migration time;
   pooling the data into the plurality of bins; and
   constructing an electropherogram, whereby signal to noise and resolution have been improved by the pooling of data into the bins.

2. A method as in claim 1 wherein the bins each is made up of time intervals of equal sizes, and the size of each bin is chosen such that the number of time intervals in the consecutive bins follows an arithmetic series.

3. A method as in claim 2 wherein the average migration time of the respective bin is approximately proportional to the square of the respective number of the respective bin.

4. A method as in claim 1 further comprising the step of filtering the binned data by Fourier transformation.

5. A method of electrophoresis analysis comprising the steps of:
   performing electrophoresis on a sample to separate it into its species;
   migrating the species past a detector which detects the presence of the species in sequence;
   providing an output of the detector in the form of data with respect of migration time;
   choosing a plurality of bins in a memory, each of a size corresponding to a range of migration time, wherein the sizes of the bins increase progressively at higher migration time;
   pooling the data into the plurality of bins; and
   constructing an electropherogram, whereby signal to noise and resolution have been improved by the pooling of data into the bins.

6. A method as in claim 5 wherein the bins each is made up of time intervals of equal sizes, and the size of each bin is chosen such that the number of time intervals in the consecutive bins follows an arithmetic series.

7. A method as in claim 6 wherein the average migration time of the respective bin is approximately proportional to the square of the respective number of the respective bin.

8. A method as in claim 5 further comprising the step of filtering the binned data by Fourier transformation.

9. A system for electrophoresis comprising:
   means for performing electrophoresis on a sample to separate it into its species;
   a detector for detecting the presence of the species and for producing corresponding data with respect to migration time;
   means for migrating the species past the detector so as to detect the presence of the species in sequence;
   data storage;
   means for choosing a plurality of bins in the data storage, each of a size corresponding to a range of migration time, wherein the sizes of the bins increases progressively at higher migration time;
   means for pooling the data into the plurality of bins; and
   means for constructing an electropherogram, whereby signal to noise and resolution have been improved by the pooling of data into the bins.

10. An apparatus as in claim 9 wherein the bins each is made up of time intervals of equal sizes, and the size of each bin is chosen such that the number of time intervals in the consecutive bins follows an arithmetic series.

11. An apparatus as in claim 10 wherein the average migration time of the respective bin is approximately proportional to the square of the respective number of the respective bin.

12. An apparatus as in claim 10 further comprising means for filtering binned data by Fourier transformation.

13. A method of analyzing data obtained by electrophoresis of sequenced DNA fragments comprising the steps of:
   choosing a plurality of bins each of a size corresponding to a range of migration time, wherein the sizes of the bins increases progressively at higher migration time;
   pooling the data into the plurality of bins;
   constructing an electropherogram, whereby signal to noise and resolution have been improved by the pooling of data into the bins; and identifying peaks in the electropherogram to determine the sequence of the DNA fragments.

14. A method as in claim 13 wherein the bins each is made up of time intervals of equal sizes, and the size of each bin is chosen such that the number of time intervals in the consecutive bins follows an arithmetic series.

15. A method as in claim 14 wherein the average migration time of the respective bin is approximately proportional to the square of the respective number of the respective bin.

16. A method as in claim 13 further comprising the step of filtering the binned data by Fourier transformation.

17. A method of identifying sequenced DNA fragments comprising the steps of:
performing electrophoresis on the sequenced DNA fragments to separate the fragments;
migrating the fragments to move past a detector which detects the presence of the fragments;
providing an output of the detector in the form of data with respect to migration time;
choosing a plurality of bins each of a size corresponding to a range of migration time, wherein the sizes of the bins increases progressively at higher migration time;
pooling the data into the plurality of bins;
constructing an electropherogram, whereby signal to noise and resolution have been improved by the pooling of data into the bins; and
identifying peaks in the electropherogram to determine the sequence of the fragments.

18. A method as in claim 17 wherein the bins each is made up of time intervals of equal sizes, and the size of each bin is chosen such that the number of time intervals in the consecutive bins follows an arithmetic series.

19. A method as in claim 18 wherein the average migration time of the respective bin is approximately proportional to the square of the respective number of the respective bin.

20. A method as in claim 17 further comprising the step of filtering the binned data by Fourier transformation.

* * * * *